(12) United States Patent
Maurer et al.

(10) Patent No.: US 9,228,155 B2
(45) Date of Patent: Jan. 5, 2016

(54) PLASTICIZERS MADE FROM OIL EXTRACTED FROM MICROORGANISMS AND POLAR POLYMERIC COMPOSITIONS COMPRISING THE SAME

(75) Inventors: Brian R. Maurer, Skillman, NJ (US); Robert F. Eaton, Belle Mead, NJ (US); Dirk B. Zinkweg, Katy, TX (US); Suh Joon Han, Belle Mead, NJ (US)

(73) Assignee: Dow Global Technologies LLC, Midland, MI (US)

( * ) Notice: Subject to any disclaimer, the term of this patent is extended or adjusted under 35 U.S.C. 154(b) by 378 days.

(21) Appl. No.: 13/812,306

(22) PCT Filed: Jul. 28, 2011

(86) PCT No.: PCT/US2011/045653
§ 371 (c)(1),
(2), (4) Date: Jan. 25, 2013

(87) PCT Pub. No.: WO2012/015997
PCT Pub. Date: Feb. 2, 2012

(65) Prior Publication Data
US 2013/0123408 A1   May 16, 2013

Related U.S. Application Data

(60) Provisional application No. 61/368,407, filed on Jul. 28, 2010.

(51) Int. Cl.
| C11C 3/00 | (2006.01) |
| C07C 69/80 | (2006.01) |
| C07D 303/02 | (2006.01) |
| C11B 3/00 | (2006.01) |
| C08K 5/04 | (2006.01) |
| C08K 5/103 | (2006.01) |
| C08K 5/1515 | (2006.01) |
| C08K 5/00 | (2006.01) |
| C08L 9/02 | (2006.01) |

(52) U.S. Cl.
CPC . *C11C 3/00* (2013.01); *C07C 69/80* (2013.01); *C07D 303/02* (2013.01); *C08K 5/04* (2013.01); *C08K 5/103* (2013.01); *C08K 5/1515* (2013.01); *C11B 3/00* (2013.01); *C08K 5/0008* (2013.01); *C08L 9/02* (2013.01)

(58) Field of Classification Search
CPC ........ C11C 3/00; C07C 69/80; C07D 303/02; C11B 3/00
USPC ........... 524/313; 554/161, 116, 175; 549/513, 549/541
See application file for complete search history.

(56) References Cited

U.S. PATENT DOCUMENTS

| 2,397,592 A | 4/1936 | Blades |
| 2,403,215 A | 7/1946 | Foster |
| 2,458,484 A | 1/1949 | Terry et al. |
| 2,500,918 A | 3/1950 | Rueter et al. |
| 2,618,622 A | 11/1952 | Grummitt et al. |
| 2,666,752 A | 1/1954 | Grummitt et al. |
| 3,138,566 A | 6/1964 | Arnold |
| 3,409,580 A | 11/1968 | Alzner et al. |
| 3,639,318 A | 2/1972 | Tijunelis et al. |
| 3,668,091 A | 6/1972 | French et al. |
| 3,712,875 A | 1/1973 | Tijunelis |
| 3,778,465 A | 12/1973 | Barnstorf |
| 3,780,140 A | 12/1973 | Hammer |
| 3,868,341 A | 2/1975 | Sauer et al. |
| 3,872,187 A | 3/1975 | Fath |
| 3,891,694 A | 6/1975 | Mills et al. |
| 4,083,816 A | 4/1978 | Frankel et al. |
| 4,346,145 A | 8/1982 | Choi et al. |
| 4,421,886 A | 12/1983 | Worschech et al. |
| 4,426,477 A | 1/1984 | Yasumatsu et al. |
| 4,556,694 A | 12/1985 | Wallace |
| 4,605,694 A | 8/1986 | Walker |
| 4,612,192 A | 9/1986 | Scheuffgen et al. |
| 4,613,533 A | 9/1986 | Loomis et al. |
| 4,627,993 A | 12/1986 | Loomis |
| 4,670,494 A | 6/1987 | Semenza, Jr. |
| 4,857,600 A | 8/1989 | Gross et al. |
| 5,225,108 A | 7/1993 | Bae et al. |
| 5,227,417 A | 7/1993 | Krousl |

(Continued)

FOREIGN PATENT DOCUMENTS

| CA | 1188445 | 6/1985 |
| CN | 1341681 | 3/2002 |

(Continued)

OTHER PUBLICATIONS

Sheehan et al. ("A Look Back at the U.S. Dept. of Energy's Aquatic Species Program—Biodiesel from Algae", National Renewable Energy Laboratory, Colorado, Jul. 1998).*

(Continued)

*Primary Examiner* — Ling Choi
*Assistant Examiner* — Ronald Grinsted
(74) *Attorney, Agent, or Firm* — Whyte Hirschboeck Dudek S.C.

(57) ABSTRACT

Plasticizers are made from oil with a narrowed, fatty acid polydispersity and extracted from a microorganism, such as a natural or genetically modified bacterium or algae. These plasticizers can comprise either a large content of either saturated C4 and/or C6 triglycerides or unsaturated C12 or greater triglycerides that have been chemically modified by one or more of epoxidation, acylation and esterification. The plasticizers of this invention are particularly well-suited for use with polar polymeric resins such as PVC.

7 Claims, 4 Drawing Sheets

(56) References Cited

U.S. PATENT DOCUMENTS

| | | | |
|---|---|---|---|
| 5,246,783 | A | 9/1993 | Spenadel et al. |
| 5,270,366 | A | 12/1993 | Hein |
| 5,278,236 | A | 1/1994 | Case et al. |
| 5,430,108 | A | 7/1995 | Schlosberg et al. |
| 5,454,806 | A | 10/1995 | Shinonome |
| 5,464,903 | A | 11/1995 | Hofmann |
| 5,466,267 | A | 11/1995 | Baillargeon et al. |
| 5,495,033 | A | 2/1996 | Basu et al. |
| 5,575,965 | A | 11/1996 | Caronia et al. |
| 5,736,605 | A | 4/1998 | Oshima |
| 5,756,570 | A | 5/1998 | Hoch et al. |
| 5,886,072 | A | 3/1999 | Linsky et al. |
| 6,063,846 | A | 5/2000 | Weng et al. |
| 6,114,425 | A | 9/2000 | Day et al. |
| 6,274,750 | B1 | 8/2001 | Sato et al. |
| 6,417,260 | B1 | 7/2002 | Weng et al. |
| 6,437,170 | B1 | 8/2002 | Thil et al. |
| 6,451,958 | B1 | 9/2002 | Fan et al. |
| 6,496,629 | B2 | 12/2002 | Ma et al. |
| 6,608,142 | B1 | 8/2003 | Weng et al. |
| 6,706,815 | B2 | 3/2004 | Marchand et al. |
| 6,714,707 | B2 | 3/2004 | Rossi et al. |
| 6,734,241 | B1 | 5/2004 | Nielsen et al. |
| 6,797,753 | B2 | 9/2004 | Benecke et al. |
| 6,849,694 | B2 | 2/2005 | Hata |
| 6,949,597 | B2 | 9/2005 | Nielsen et al. |
| 7,700,675 | B2 | 4/2010 | Bueno de Almeida et al. |
| 2002/0013396 | A1 | 1/2002 | Benecke et al. |
| 2004/0122159 | A1 | 6/2004 | Mhetar et al. |
| 2005/0090590 | A1 | 4/2005 | Nielsen et al. |
| 2005/0203230 | A1 | 9/2005 | Kadakia et al. |
| 2006/0025544 | A1 | 2/2006 | Koube et al. |
| 2006/0276575 | A1 | 12/2006 | Hamaguchi et al. |
| 2007/0100049 | A1 | 5/2007 | Ishizuka et al. |
| 2007/0135562 | A1 | 6/2007 | Freese et al. |
| 2008/0200595 | A1 | 8/2008 | Hinault et al. |
| 2008/0227993 | A1 | 9/2008 | Zuckerman |
| 2009/0149585 | A1 | 6/2009 | DeQuadros Junior et al. |
| 2009/0149586 | A1 | 6/2009 | DeQuadros Junior et al. |
| 2009/0312478 | A1 | 12/2009 | Hasegawa et al. |
| 2010/0010127 | A1* | 1/2010 | Barki et al. .......... 524/114 |
| 2010/0256278 | A1 | 10/2010 | Harada et al. |
| 2011/0076502 | A1 | 3/2011 | Chaudhary et al. |
| 2011/0272174 | A1 | 11/2011 | Chaudhary et al. |
| 2013/0005937 | A1 | 1/2013 | Cramail et al. |

FOREIGN PATENT DOCUMENTS

| | | |
|---|---|---|
| CN | 101070510 | 11/2007 |
| CN | 101108982 | 1/2008 |
| CN | 101591588 | 12/2009 |
| CN | 101824193 | 9/2010 |
| CN | 101914219 | 12/2010 |
| EP | 0192961 A1 | 9/1986 |
| EP | 0358179 A2 | 3/1990 |
| EP | 0364717 A1 | 4/1990 |
| EP | 0393813 A1 | 10/1990 |
| EP | 0473915 A1 | 3/1992 |
| EP | 0565984 A1 | 10/1993 |
| EP | 1361039 | 11/2003 |
| EP | 0986606 B1 | 8/2004 |
| EP | 1218443 | 10/2005 |
| EP | 1624014 | 8/2006 |
| EP | 2070977 A2 | 6/2009 |
| EP | 2245089 A1 | 5/2012 |
| FR | 1437722 | 5/1966 |
| GB | 499931 | 1/1939 |
| GB | 790314 | 2/1958 |
| GB | 910543 | 11/1962 |
| GB | 934689 | 8/1963 |
| GB | 1022920 | 3/1966 |
| GB | 1102506 | 2/1968 |
| GB | 1300526 | 12/1972 |
| GB | 1341623 | 12/1973 |
| GB | 1415770 | 11/1975 |
| GB | 2155021 | 9/1985 |
| JP | S61-016950 | 1/1986 |
| JP | S63175056 A | 7/1988 |
| JP | S63182366 A | 7/1988 |
| JP | 04-059851 | 2/1992 |
| JP | H04-085354 | 3/1992 |
| JP | H04-261452 | 9/1992 |
| JP | 2000-319468 | 11/2000 |
| JP | 2003-064233 | 3/2003 |
| JP | 2003-297149 | 10/2003 |
| JP | 2004311064 | 11/2004 |
| JP | 2005041980 A | 2/2005 |
| JP | 2010-042669 | 2/2010 |
| WO | 9730115 | 8/1997 |
| WO | 0114466 | 3/2001 |
| WO | 01/98404 | 12/2001 |
| WO | 2004/052977 A1 | 6/2004 |
| WO | 2007006489 | 1/2007 |
| WO | 2008081330 | 7/2008 |
| WO | 2008081332 | 7/2008 |
| WO | 2008/122364 A1 | 10/2008 |
| WO | 2009/102877 | 8/2009 |
| WO | 2011/041372 | 4/2011 |
| WO | 2011/041380 | 4/2011 |
| WO | 2011/041388 | 4/2011 |
| WO | 2013003225 A2 | 1/2013 |

OTHER PUBLICATIONS

TCI America—Tributyrin (http://web.archive.org/web/20080411112145/http://tciamerica.com/catalog/T0364.html—Apr. 2008).*
Danisco, Grindsted Soft-n-Safe brochure (date unknown).
Orellana-Coca et al., Journal of Molecular Catalysis B: Enzymatic 44 (2007) 133-137.
Du et al., JAOCS, vol. 81, No. 4 (2004) 477-480.
Sheehan et al, A Look Back at the U.S. Department of Energy's Aquatic Species Program: Biodiesel from Algae, National Renewable Energy Laboratory, Colorado, Jul. 1998, pp. 1-294.
Greenspan et al., Industrial and Engineering Chemistry, 445(12), 1953, pp. 2722-2726.
Thomson Scientific, Mar. 13, 2009, London, GB.
Gan et al., European Polymer Journal, 31(8), 1994, pp. 719-724.
Rehberg et al., Ind. Eng. Chem., 44(9) 1952, pp. 2191-2195.
Tekin et al., JAOCS, 77(3), 2000, pp. 281-283.
Cai et al., Eur. J. Lipid Sci., Technol., 2008, 110, pp. 341-346.
Campanella et al., Chemical Engineering Journal, 144 (2008), pp. 466-475.
Santacesara et al, Chemical Engineering Journal, vol. 173, Issue 1, Sep. 1, 2011, pp. 198-209.
Senzana et al, Journal of the Americal Oil Chemists Society, vol. 78, No. 7 (2001), pp. 725-731.
Haas, Fuel Processing Technology 86, 2005, pp. 1087-1096.
Freedman et al., JAOCS, 63(10), 1986, pp. 1375-1380.
Morgenstern, B., Epoxidized Fatty Acid Esters as Plasticizers for PVC, presented at the 7th Freiberg Polymer Conference, Apr. 21 and 22, 2005.
Morgenstern, B., Use of Modified Fatty Acid Esters as Plasticizers for PVC dated Sep. 12, 2003.
Morgenstern, B., Epoxidized Fatty Acid Esters as Plasticizers for PVC dated Apr. 22, 2005.
Opposition filed against EP2245089 dated Jan. 9, 2013.
http://hebjingu.en.alibaba.com.
http://en.wikipedia.org/wiki/Chlorine.
http://en.wikipedia.org/wiki/Bleaching_of_wood_pulp.
TIC America, Online catalog: Tributrin; http://web.archive.org/web/20080511154307/http://www.tciamerica.com/.
International Search Report and Written Opinion of PCT/US2009/033935 dated May 18, 2009.
International Preliminary Report on Patentability of PCT/US2009/033935 dated Aug. 26, 2010.
International Search Report and Written Opinion of PCT/US2010/050654 dated Nov. 9, 2010.

(56) References Cited

OTHER PUBLICATIONS

International Search Report and Written Opinion of PCT/US2010/050676 dated Jan. 12, 2011.
International Preliminary Report on Patentability of PCT/US2011/041557 dated Aug. 31, 2012.
International Search Report and Written Opinion of PCT/US2011/041557 dated Sep. 5, 2011.
International Preliminary Report on Patentability of PCT/US2011/050690 dated Jan. 12, 2012.
International Search Report and Written Opinion of PCT/US2011/045653 dated Oct. 7, 2011.
International Search Report and Written Opinion of PCT/US2012/043740 dated Jan. 23, 2013.
International Search Report and Written Opinion of PCT/US2012/055070 dated Dec. 3, 2012.
International Search Report and Written Opinion of PCT/US2013/023362 dated Mar. 28, 2013.
International Search Report and Written Opinion of PCT/US2010/050699 dated Nov. 8, 2010.
International Search Report and Written Opinion of PCT/US2011/035143 dated Aug. 26, 2011.
International Search Report and Written Opinion of PCT/US2010/050690 dated Feb. 8, 2011.
Greenspan et al., The Journal of the American Oil Chemists Society, 33, 1956, pp. 391-394.
Taylor, Proceedings of the World Conference on Oilseed Technology and Utilization, American Oil Chemists Society, Champaign, 1992, pp. 152-165.
Vertellus Performance Materials Inc.; Flexricin P-8 Technical Data Sheet, Nov. 2006.
Grummitt et al., Acetylated Castor Oil Industrial and Engineering Chemistry, vol. 37, No. 5, May 1945, pp. 485-491.

\* cited by examiner

US 9,228,155 B2

PLASTICIZERS MADE FROM OIL EXTRACTED FROM MICROORGANISMS AND POLAR POLYMERIC COMPOSITIONS COMPRISING THE SAME

CROSS REFERENCE TO RELATED APPLICATION

The present application is the national phase of PCT Patent Application No. PCT/US2011/045653 filed Jul. 28, 2011, which claims the benefit of U.S. Ser. No. 61/368,407, filed Jul. 28, 2010; which application is fully incorporated herein by reference.

BACKGROUND OF THE INVENTION

1. Field of the Invention

This invention relates to plasticizers. In one aspect the invention relates to plasticizers derived from bio-sources while in another aspect, the invention relates to plasticizers derived from microorganisms such as bacteria and algae. In yet another aspect the invention relates to plasticizers derived from genetically modified microorganisms while in still another aspect, the invention relates to compositions comprising such a plasticizer and a polar polymeric resin.

2. Description of the Related Art

Plasticizers are compounds or mixtures of compounds that are added to polymer resins to impart softness and flexibility. Phthalic acid diesters (also known as "phthalates") are well-known petroleum-derived plasticizers that are widely used in many flexible polymer products, such as polymer products formed from polyvinyl chloride (PVC) and other polar polymers. Known petroleum-derived plasticizers also include trimellitates and adipic polyesters both typically used in high temperature applications. Mixtures of plasticizers are often used to obtain optimum properties.

Petroleum-derived plasticizers, particularly the phthalate plasticizers, however have come under intense scrutiny by public interest groups that are concerned about their negative environmental impact and potential adverse health effects in humans (especially children). As such, plasticizers derived from other sources have become of great interest, particularly those derived from seeds and nuts. Exemplary sources include but are not limited to oils derived from soy bean, linseed, tung seed, coconut, palm, olive, cotton seed, oiticica seed and castor bean. One example of such a plasticizer is soy-derived epoxy fatty acid methyl ester or e-FAME. Plasticizers derived from seed and nut sources have proved effective but here too, they come with problems.

One such problem is that these plant-derived plasticizers are mixtures of a number of different compounds not all of which are necessary or beneficial to the function of plasticizing. For example, soy oil comprises palmitic, stearic, oleic, linoleic, linolenic and higher molecular weight (more carbon atoms) fatty acids only some of which can be converted to a methyl ester and the double bonds epoxidized to make e-FAME. Palmitic and stearic acids are saturated, i.e., are without double bonds, and as such, they cannot be epoxidized. These saturated fatty acid esters have very low solubility in PVC and other polar vinyl polymers, and they tend to precipitate out of the liquid plasticizer on standing at ambient temperature (23° C.). Fatty acids with 22 or more carbon atoms, even with multiple double bonds and after epoxidation, also exhibit solubility issues.

Another problem with the use of seed- and nut-derived plasticizers is they divert the use of these materials from dietary uses, and this imparts upward pressure on the costs of many food products.

SUMMARY OF THE INVENTION

In one embodiment the invention is oil with a narrowed, fatty acid polydispersity and extracted from a microorganism, natural or genetically modified, particularly a microorganism such as a bacterium or algae.

In one embodiment the invention is a plasticizer made from oil with a narrowed, fatty acid polydispersity and extracted from a microorganism, natural or genetically modified, particularly a microorganism such as a bacterium or algae.

In one embodiment the plasticizer is an oil that consists essentially of saturated $C_4$ and/or $C_6$ triglycerides.

In one embodiment the plasticizer is an oil that comprises unsaturated $C_{12}$ or greater triglycerides and in which the unsaturated $C_{12}$ or greater triglycerides are chemically modified.

In one embodiment the unsaturated $C_{12}$ or greater triglycerides are chemically modified by at least one of epoxidation, acylation and esterification.

In one embodiment the unsaturated triglycerides are $C_{16}$-$C_{20}$ unsaturated triglycerides.

In one embodiment the triglycerides are converted to fatty acid esters.

In one embodiment the invention is a plasticizer made from oil with a narrowed, fatty acid polydispersity and extracted from a microorganism, particularly a microorganism such as a bacterium or algae, natural or genetically modified, the oil having been subjected to at least one of epoxidation, acylation and esterification. In one embodiment the invention is e-FAME made from oil with a narrowed, fatty acid polydispersity and extracted from a microorganism, particularly a microorganism such as a bacterium or algae, natural or genetically modified.

In one embodiment the invention is a plasticizer made from oil with a narrowed, fatty acid polydispersity and extracted from a microorganism, particularly a microorganism such as a natural or genetically engineered bacterium or algae, the plasticizer having at least one, preferably at least two, more preferably at least three and even more preferably all four, of (i) a solubility in PVC of greater than 40 parts per hundred resin (phr) at 90° C., (ii) liquidity at ambient temperature (23° C.), (iii) a weight average molecular weight (Mw) of 250 or greater, and (iv) an iodine number of 10 or less.

In one embodiment the invention is a polymeric composition comprising a polar polymeric resin and a plasticizer made from oil with a narrowed, fatty acid polydispersity and extracted from a microorganism, particularly a microscopic organism such as a natural or genetically engineered bacterium or algae. In one embodiment the polymeric resin is PVC or other vinyl chloride polymer.

In one embodiment the invention is a polymeric composition comprising PVC and a plasticizer made from oil with a narrowed, fatty acid polydispersity and extracted from a microorganism, particularly a natural or genetically modified microorganism such as a genetically engineered bacterium or algae, the plasticizer having at least one, preferably at least two, more preferably at least three and even more preferably all four, of (i) a solubility in PVC of greater than 40 parts per hundred resin (phr) at 90° C., (ii) liquidity at ambient temperature (23° C.), (iii) a weight average molecular weight (Mw) of 250 or greater, and (iv) an iodine number of 10 or less. In one embodiment the composition has a glass transition temperature (Tg) of 50° C. or less.

In other embodiments the oil with a narrowed, fatty acid polydispersity and extracted from a microorganism can be designed to balance hydrophobicity and polarity so as to maximize the solubility of a plasticizer made from the oil relative to the polar polymeric resin into which it is incorporated. For example, oil derived from a genetically modified bacterium or algae can comprise a triglyceride with 10 carbon atoms and one epoxy group per $C_{10}$ chain or it can comprise two engineered fatty acids with three epoxy groups reacted with a diol that has several methylene ($-CH_2-$) groups. Both engineered oils would exhibit good solubility in PVC.

Upon epoxidation, oils with little or no saturated fatty acid content not only exhibit improved solubility in polar polymeric resins, e.g., PVC, but they also exhibit a reduced tendency to precipitate from solution upon standing at ambient conditions (23° C. and atmospheric pressure).

DETAILED DESCRIPTION OF THE PREFERRED EMBODIMENT

Definitions

Figure 1:
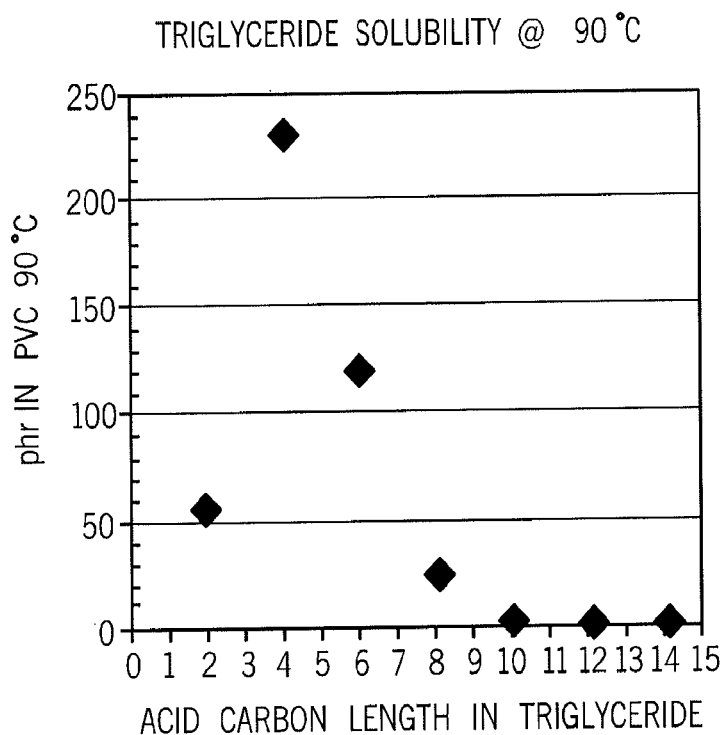
FIG. 1 is a plot of the triglyceride solubility in parts per hundred resin (phr), parts of solute per 100 parts of PVC by weight, as a function of the number of carbons in the fatty acids of triglyceride.

Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, melt index, etc., is from 100 to 1,000, then the intent is that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the amounts for components in the composition and the various characteristics and properties by which these components are defined.

As used with respect to a chemical compound, unless specifically indicated otherwise, the singular includes all isomeric forms and vice versa (for example, "hexane", includes all isomers of hexane individually or collectively).

The terms "comprising", "including", "having" and their derivatives are not intended to exclude the presence of any additional component, step or procedure, whether or not the same is specifically disclosed. In order to avoid any doubt, all compositions claimed through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

"Composition" and like terms mean a mixture or blend of two or more components.

"Oil" and like terms mean compositions comprising mostly, if not exclusively, triglycerides. Oils are typically, but not necessarily, liquid under ambient conditions.

"Engineered oil" and like terms mean oil extracted from a genetically engineered microorganism.

"Oil with a narrowed, fatty acid polydispersity" and like terms mean that the oil comprises little, e.g., less than five, preferably less than one, weight percent, if any, saturated fatty acid and/or little, e.g., less than five, preferably less than one, weight percent, if any, fatty acid with 20 or more carbon atoms. Preferably, the oil comprises only fatty acids of 16-20 carbon atoms all of which comprise at least one, preferably at least two, double bonds. Oil with a narrowed, fatty acid polydispersity comprising more than 80, preferably more than 90 and even more preferably more than 95, weight percent linoleic acid is the preferred oil for making the plasticizers of this invention.

"Natural or genetically modified microorganism" and like terms mean a microorganism as found in nature or for which the genetic code has been manipulated by human intervention in a manner that does not occur under natural conditions. Typically these are microscopic organisms such as bacteria, algae, yeast, molds, slime, plankton and other such life forms. For purposes of this invention, these microorganisms do not include traditional plant and animal sources of fatty acid oil such as soy bean, linseed, tung seed, coconut, palm olive, olive, cotton seed, oiticica seed, castor bean, fish, marine mammals and farm animals, e.g., cattle and pigs. Preferred microorganisms are bacteria and algae.

"Polar polymeric resins" and like terms mean a polymer that includes one or more polar groups (sometimes referred to as polar functionalities). A "polar group," means any group that imparts a bond dipole moment to an otherwise essentially nonpolar polymeric molecule. Exemplary polar groups include carbonyls, carboxylic acid groups, carboxylic acid anhydrate groups, carboxylic ester groups, epoxy groups, sulfonyl groups, nitrile groups, amide groups, silane groups and the like, and these groups can be introduced into the polymer either through grafting or copolymerization.

Microorganisms

The microorganisms used in the practice of this invention are naturally occurring microorganisms that produce an oil, or are microorganisms genetically engineered to produce an engineered oil, with a large content of unsaturated fatty acids, preferably with two or more, more preferably just two, double bonds, and little, if any, saturated fatty acids. If genetically modified, the genetic code manipulation is performed using materials and techniques known to those skilled in the art of recombinant DNA.

The oil produced by the microorganism is collected also using known materials and known techniques. The oil comprises one or more fatty acids of which most, if not all, are unsaturated and preferably most, if not all, of the unsaturated fatty acids contain at least two, more preferably just two, double bonds. Most preferably, the oil comprises a single fatty acid containing two double bonds. Representative, but not limiting, fatty acids comprising the oil include oleic acid (one double bond), linoleic acid (two double bonds), and linolenic acid (three double bonds), with linoleic the preferred fatty acid.

Converting Oil to Plasticizer

For the oils derived from the microorganisms to be useful plasticizers for PVC and other polar polymers, the oils must exhibit both low volatility and good solubility in the polymer. Low volatility means that the oil is not prone to evaporate from the polar polymer over time and under normal use conditions of the polymer or, in other words, the oil exhibits permanency within the polymer. Good solubility means that the oil initially mixes well with the polar polymer and once well mixed with the polymer, it will not precipitate out of the polymer to any significant degree upon standing at ambient temperature (23° C.) over an extended period of time, e.g., the expected useful life of the polymer in its (the polymer's) intended end use.

Measures of volatility and solubility of an oil for use as a plasticizer in PVC and other polar polymers include solubility in PVC at 90° C., liquidity at ambient conditions, Mw and iodine number (all measured using conventional procedures). In one embodiment, oil extracted from a microorganism is a useful plasticizer for PVC or other polar polymer, particularly other halogenated vinyl polymers, if the oil has at least one, preferably at least two, more preferably at least three and even more preferably all four, of (i) a solubility in PVC of greater than 40 phr at 90° C., (ii) liquidity at ambient temperature and pressure (23° C., atmospheric), (iii) a Mw of 250 or greater, and (iv) an iodine number of 10 or less. In one embodiment the oil has properties (i) and (ii), or (i) and (iii), or (i) and (iv), or (ii) and (iii), or (ii) and (iv), or (iii) and (iv). In one embodiment, the oil has properties (i), (ii) and (iii), or (i), (iii) and (iv), or (ii), (iii) and (iv).

In one embodiment, the plasticizers of this invention can consist essentially of oils of $C_4$ and/or $C_6$ saturated triglycerides, and these oils can be used without chemical modification as described below. These oils are of sufficiently low volatility and of sufficiently high solubility that they can be used as extracted (perhaps subject to one or more purification procedures) from the microorganism.

Plasticizers made from other oils, however, particularly unsaturated oils comprising, if not consisting of, triglycerides of twelve or more carbon atoms ($C_{12}$ or greater), typically sixteen to twenty carbon toms ($C_{16}$ to $C_{20}$) and more typically of eighteen carbon atoms ($C_{18}$), are likely to require one or more chemical modifications of the oil before acquiring one or more of properties (i)-(iv) described above. Such oil recovered from the microorganism is typically subjected to at least one of acylation, epoxidation and esterification. Acylation is the process of introducing an acyl group into the molecule of a compound having a hydroxyl group (—OH). In other words, acylation replaces the hydrogen of the —OH group with a RCO— group. Nonlimiting examples of suitable acylation reagents include acetic anhydride and acetyl chloride.

Epoxidation is the process of converting a double bond into an epoxide. An "epoxide group" is a three-membered cyclic ether (also called oxirane or an alkylene oxide) in which an oxygen atom is joined to each of two carbon atoms that are already bonded to each other. The term "epoxidized fatty acid ester" means a compound with at least one fatty acid moiety which contains at least one epoxide group. Nonlimiting examples of suitable epoxidized fatty acid esters include epoxidized propylene glycol dioleate and epoxidized fatty acid methyl esters.

The epoxidized fatty acid ester can be prepared in a variety of ways. For example, the algae- or bacteria-sourced oil can be used as the starting material. In this instance, the oil may be saponified to the fatty acids and then esterified with alcohols. Next, the low molecular weight esters are epoxidized. The unsaturated ester can be epoxidized with a per-acid.

One nonlimiting example for the preparation of an epoxide of a fatty acid methyl ester begins with oil from a bacteria or algae, natural or genetically engineered, in which the oil is transesterified with methanol to make the methyl ester of the fatty acids in the oil. Glycerol is removed from the reaction products due to its insolubility. A solution of per-acetic acid in ethyl acetate is used to epoxidize the double bonds on the fatty acids. The per-acid is kept below 35% per-acid and 35° C. to prevent detonation. After completion, the ethyl acetate and product acetic acid are removed via vacuum stripping.

In one embodiment the epoxidized fatty acid ester can be any epoxidized fatty acid $C_1$-$C_{14}$ ester, including methyl, ethyl, propyl, butyl, and 2-ethylhexyl esters. In one embodiment the epoxidized fatty acid ester is an epoxide of a fatty acid methyl ester.

Esterification is a process in which two reactants, typically an acid and an alcohol, are reacted with one another to form an ester. Transesterification is the process of exchanging the organic group R" of an ester with the organic group R' of an alcohol. The fatty acids of the oils of this invention can be converted to esters by transesterification. For example, oil containing two or three double bonds can be transesterified with methanol, with or without a catalyst, to the methyl ester and then epoxidized to give a lower molecular weight plasticizer. The conventional method to make saturated fatty acid free esters involves distillation of methyl esters to get the desirable two or three double bond containing fatty acid esters. Thus, the extra step is eliminated by using the oils derived from the genetically engineered organisms used in the practice of this invention.

In another embodiment the epoxidized oil can be transesterified with methanol and a base catalyst, e.g., sodium methoxide, to give an epoxidized methyl ester. Transesterification is not limited to methyl esters, and higher molecular weight mono, di and polyhydroxy alcohols can be used to make various desirable products.

Moreover, naturally occurring epoxidized oil can increase the epoxy groups in the oil structure through genetic engineering. For example, *Vernonia anthelmintica* can be genetically modified to produce an oil with more epoxy groups, and not only would this enhance the solubility of the oil in polymers like PVC, but it also eliminates the need to epoxidize the oil thus saving a step in the process of making a plasticizer. Solubility of oils like soy oil in PVC is increased many fold by epoxidation. Solubility of soy oil in PVC is increased by a factor of up to 150 by epoxidation to 7% oxirane oxygen content.

Typically and preferably the plasticizers of this invention are sufficiently soluble in PVC to be 'permanent', i.e., they will remain within the polymer matrix for an extended period of time under both typical storage and use conditions. Most studies of PVC (and other polymer) plasticizers use an empirical approach and do not account for this fundamental issue.

Polarity of an unsaturated triglyceride can be increased by epoxidation making a poorly soluble (90° C. solubility which is well below that of the phthalates and trimelitates) material into a much more soluble and thus viable plasticizer. Just adding polarity can hurt PVC solubility: Hydroxy groups, while very polar, result in poor PVC solubility for the alcohol-containing plasticizers. Ricinoleic acid is an example of a naturally occurring fatty acid which contains —OH groups. Capping the —OH groups with an acid to make an ester will improve solubility. Preferred polar groups include esters and epoxies. Mustard-like plants, and especially *Vernonia* and *Euphorbia* plants, make epoxies naturally. Genetic material from these plants can be used to grow modified algae-containing epoxies. Alternately, unsaturated oils from algae can be epoxidized via peroxides and per-acids to convert poorly soluble algae oil in to an effective plasticizer.

Once the appropriate oils have been grown, they can be transesterified with various alcohols to build esters like epoxidized fatty acid methyl-esters with even better PVC solubility. Other esters like a 2-ethylhexyl ester can be made from either the oil or the methyl ester giving a product with enhanced low temperature PVC flexibility. The derived fatty acid methyl esters can be transesterified with diols and other multifunctional alcohols to give more or less volatile plasticizers or plasticizers with unique properties.

Typically and preferably, the plasticizers of this invention, i.e., plasticizers (i) derived from natural or genetically modified microorganisms, and (ii) that may or may not have been subjected to chemical modification, e.g., epoxidation, have a glass transition temperature, Tg, below that of the polar polymer, e.g., below that of PVC. Typically and preferably, the plasticizers of this invention reduce the Tg of the PVC from 85-90° C. to a value that makes the plasticized PVC flexible enough for the specific application. For wire and cable the Tg of the plasticized PVC is 40-50° C. Other applications may have the Tg below room temperature. The Tg of the plasticizer itself is often in the −100 to −20° C. so that the Tg of the polymer plus plasticizer composition is in the temperature range of interest, i.e., the plasticizer is usually a low Tg liquid or amorphous polymer.

The plasticizer of this invention and polar polymer are matched so that the plasticizer will not crystallize on aging within the polymer matrix. Crystallization of the plasticizer reduces or eliminates the effect of the plasticizer thus returning the polymer to or near its pre-plasticization condition.

The plasticizers of this invention are sufficiently stable, i.e., nonvolatile, so that they exhibits a permanency or effectiveness over the life of the plastic.

The plasticizers of this invention exhibit oxidative stability. In terms of iodine number, these plasticizers have a low iodine number, e.g., 10 or less, preferably 5 or less and even more preferably 2 or less. Iodine number is a measure of the unsaturation of a polymer, e.g., the number of its double bonds. Plasticizers with an iodine number greater than 10 can turn dark in color and gel.

Crosslinking is due to oxidation in air and subsequent chemical crosslinking as in 'oil based' coatings. Epoxidation of the double bond will both eliminate the air oxidation problem and increase solubility in PVC. Reaction of the double bond to form an aldehyde (the addition of a carbonyl group to one carbon of the previous double bond) via low-pressure, oxo-alcohol chemistry eliminates the oxidative crosslinking of the double bond. Reduction of the aldehyde to an alcohol and capping with and acid also eliminates oxidative crosslinking.

Plasticizer Compositions

The unmodified and chemically modified oils derived from the natural or genetically modified microorganisms used in the practice of this invention may be referred to as a "composition," "a plasticizer composition," or "a plasticizer." The plasticizer composition may include, based on the total weight of the plasticizer composition, from 1 weight percent (wt %) to 99 wt % of the natural and/or engineered oil and from 99 wt % to 1 wt % of one or more traditional plasticizers, e.g., e-FAME, or from 30 wt % to 99 wt % of the natural and/or engineered oil and from 70 wt % to 1 wt % of one or more traditional plasticizers, i.e., plasticizers made from a petroleum product or from an oil that does not have a narrowed, fatty acid polydispersity and was not extracted from a microorganism. These plasticizer compositions can comprise two or more natural oils and/or two or more engineered oils. These plasticizer compositions can also comprise one or more other materials as well, such as antioxidants, biocides, etc.

Plasticizer compositions lower the modulus and tensile strength, and increase flexibility, elongation, impact strength, and tear strength, of the polar polymeric resin (typically a thermoplastic polymer) to which they are added. The plasticizer may also lower the melting point of the polar polymeric resin, which lowers the Tg and enhances processability of the polar polymeric resin to which it is added.

Introduction of carboxyl groups on the fatty acid chain will allow simple epoxidation via epichlorohydrin which adds polarity and improves polymer solubility in various polymers like PVC, nitrile rubber, chlorinated polyethylene and the like. The epoxies also stabilize the PVC from dehydrochlorination. By controlling the carboxyl groups, the level of epoxidation can be optimized.

Adjacent alcohol groups can be converted to ketal structures which add polarity and PVC solubility.

Controlled functional groups on the fatty acids can be converted to derivatives which are useful in plasticized PVC and other polar polymers as noted in Organic Chemistry texts like: *Advanced Organic Chemistry Parts A and B*, 4th edition, by F A Carey and R J Sundberg, Plenum Publishers, 2000.

Polymeric Compositions

In one embodiment the invention is a polar polymeric composition comprising a polar polymeric resin and a plasticizer or plasticizer composition, i.e., oil extracted from a natural or genetically engineered microorganism or the oil in combination with one or more other plasticizers, e.g., e-FAME. The polar polymeric composition contains from 1 wt % to 99 wt % of the polar polymeric resin and from 99 wt % to 1 wt % of the plasticizer or plasticizer composition. Weight percent is based on total weight of the polar polymeric composition.

Nonlimiting examples of suitable polar polymeric resins include the polysulfides, polyurethanes (e.g., polyester polyurethanes), acrylics, epichlorohydrins, chlorosulfonated polyethylene, chlorinated polyethylene, polychloroprene, polyvinylidene chloride, nitrile rubbers (both thermoplastic and crosslinked) and chlorinated rubbers. The term "vinyl chloride resin" means is a vinyl chloride polymer, such as PVC (both crosslinked and uncrosslinked), or a vinyl chloride copolymer such as vinyl chloride/vinyl acetate copolymer, vinyl chloride/acrylate copolymer, vinyl chloride/methacrylate copolymer, vinyl chloride/vinylidene chloride copolymer, vinyl chloride/ethylene copolymer or a copolymer prepared by grafting vinyl chloride onto ethylene/vinyl acetate copolymer. The resin composition can also include a polymer blend of the above-mentioned vinyl chloride polymer or vinyl chloride copolymer with other miscible or compatible polymers including, but not limited to, chlorinated polyethylene, thermoplastic polyurethane, olefin polymers such as a methacryl polymer or acrylonitrile-butadiene-styrene polymer (ABS resin).

For a polar polymer like PVC, methyl esters of two or three epoxy groups give excellent PVC solubility. For higher molecular weight monohydroxy alcohols like 2-ethyl-hexanol, PVC solubility is enhanced with three or more epoxy groups per chain.

The polar polymeric compositions may include one or more additives such as a filler, an antioxidant, a flame retardant (antimony trioxide, molybdic oxide and alumina hydrate), a heat stabilizer, an anti-drip agent, a colorant, a lubricant, a low molecular weight polyethylene, a hindered amine light stabilizer (having at least one secondary or tertiary amine group) ("HALS"), UV light absorbers (such as o-hydroxyphenyltriazines), curing agents, boosters and retardants, processing aids, coupling agents, antistatic agents, nucleating agents, slip agents, viscosity control agents, tackifiers, anti-blocking agents, surfactants, extender oils, acid scavengers, metal deactivators, and any combination thereof. These additives are used in know amounts and in know ways.

Other Applications

For surfactant applications a hydrophobic fatty alcohol and be attached to a fatty acid modified with polar groups like epoxies, ethers and the like to make useful surfactant products.

Metal soap stabilizers for halogen polymers often comprise a metal like Zn, Ca, Ba, Pb or Cd attached to a stearate or other fatty acids. Improved stabilizers can be made by incorporating functional groups on the fatty acid as described above. The added functional groups like epoxies, carbodiimides, etc. can make dual functionalized soap stabilizers.

Specific Embodiments

Experimental

PVC powder is compression molded into clear 10-20 mil films at 180° C. Approximately one inch square samples are cut from the film. Into a half-pint, screw-top jar is placed an aluminum weighing dish. About 10-20 grams (g) of a triglyceride oil or other candidate plasticizer is added to the dish. The PVC film is weighed on an analytical balance. The PVC film is then placed in the triglyceride and put into an oven maintained at 90° C. The Tg of PVC is about 85° C. Time to equilibrium below the Tg takes years for triglyceride to slow diffuse into the PVC. Diffusion is much faster at temperatures above the Tg, e.g., weeks vs. years.

From time to time the films are removed from the oven, blotted to remove surface liquids and weighed, then returned to the triglyceride in the jar and the jar returned to the oven. After successive weighings show little change, the assumption is that equilibrium uptake of the triglyceride is obtained.

Alternatively, equilibrium uptake can be calculated by fitting a first order kinetics equation to the weight gain data to determine the equilibrium uptake after "infinite" storage time at 90° C. Cutting the PVC from films made at about the same time is useful because the solubility of the triglyceride in PVC will be function, in part, of the thermal history of the PVC film.

The triglycerides are obtained from TCI Americas and used without further purification. C12 and C14 fatty acid triglycerides are solids at ambient conditions but liquid at 90° C. and atmospheric pressure.

Results

FIG. 1 is a plot of the triglyceride solubility in parts of solute per 100 parts of PVC by weight, as a function of the number of carbons in the fatty acids of the triglyceride. Each triglyceride consisted of identical fatty acids: C2=acetate, C4=butyrate, C6=hexanoate, etc. Solubility is maximized at the butyrate ester with four carbon atoms.

Figure 2:
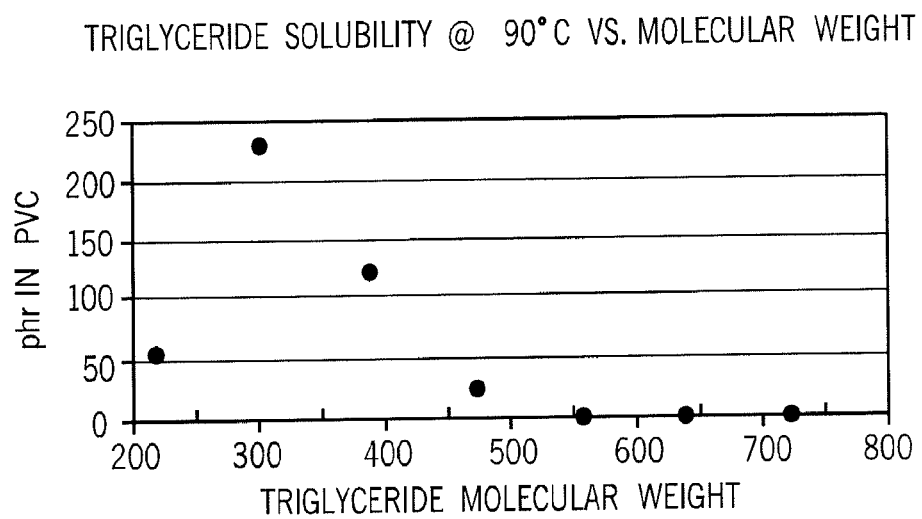
FIG. 2 is a plot reporting the solubility of triglycerides in PVC versus triglyceride molecular weight.

FIG. 2 shows solubility in PVC versus triglyceride molecular weight. As clearly evident from this plot, triglyceride solubility is not simply a function of the molecular weight of the triglyceride. The highest molecular weight glycerides are the least soluble.

Based on entropic considerations, the expectation is that the lowest molecular weight molecules will have the highest solubility, but clearly this is not the case. One significant factor in solubility is molecule polarity or, in qualitative terms, "like dissolves like" which is often expressed in terms of "solubility parameters". In the broadest sense, when the solubility parameter of the solute is equal to the solubility parameter of the polymer or solvent, the solubility in the polymer or solvent is maximized for a given molecular weight.

Solubility Parameter Calculation

Multiple ways exist to calculate solubility parameters using "group contribution" methods. Table 2 lists the chemical group, for example methyl, the type of chemical bond (saturated), the $F_T$ parameter used to calculate the total solubility parameter (see Equation 1 below), Fp polar solubility parameter contribution and $V_{T_G}$ solute molar volume at Tg.

$$\delta_{T\,Sqrt(cal/cc)} = \{[\Sigma F_T] + 135.1\}/Vm \quad \text{(Eq. 1)}$$

in which Vm=solute molar volume=Mw/ρ (density). The densities of the triglycerides tested here are available from either the supplier or the literature. Table 2 is used to calculate solubility parameters using group contributions to the total solubility parameter $\delta_T$. Results are also reported in Table 2.

TABLE 2

| | Triglyceride Properties | | | |
|---|---|---|---|---|
| Fatty Acid Carbons | Mw | P gm/cc | δ | Phr Measured @ 90° C. |
| 2 | 218 | 1.16 | 10.13 | 56.48 |
| 4 | 302 | 1.04 | 9.29 | 232.47 |
| 6 | 387 | 0.98 | 8.85 | 122 |
| 8 | 471 | 0.96 | 8.73 | 25.80 |
| 10 | 555 | 0.92 | 8.41 | 11.5 |
| 12 | 638 | 0.90 | 8.26 | 6.22 |
| 14 | 722 | 0.9* | 8.28 | 3.90 |

*estimated

Figure 3:
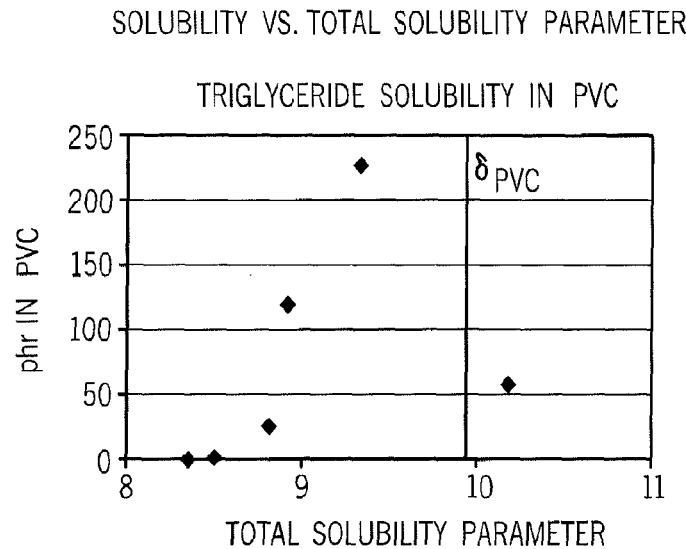
FIG. 3 is a plot reporting the solubility of triglycerides in PVC versus total solubility parameter δT.

Solubility depends on the solubility parameter for the triglyceride in $$X_{12} = (V/RT)*(\delta_{PVC} - \delta_{plasticizer})^2 \quad \text{(Eq. 2)}$$

in which V=the plasticizer molar volume (cc/mole), R=the gas constant (1.98), T=temperature in degrees Kelvin, $\delta_{PVC}$=the polymer total solubility parameter, and $\delta_{plasticizer}$=the plasticizer total solubility parameter. FIG. 3 reports the solubility versus total solubility parameter $\delta_T$.

FIGS. 1-3 show that the butyrate (C4) triglyceride has the highest PVC solubility of the triglycerides tested. This is a simple indication of the "like dissolves like" or, more quantitatively, solubility maximizes as the solubility parameter of the solute approaches that of the solvent or polymer. Broadly solubility appears to depend on both the molecular weight and solubility parameter of the solute for a given polymer. By inspection of the $X_{12}$ parameter in Equation 2, as the solubility parameters for the polymer and plasticizer get closer to each other, the $X_{12}$ decreases. Since $X_{12}$ represents a positive enthalpy of mixing, the larger $X_{12}$ is, the lower the solubility of the plasticizer in the polymer, i.e., "like dissolves like". The closer the solubility parameters, the more the polymer and plasticizer are alike. However, $X_{12}$ is directly proportional to the molar volume of the plasticizer, V, thus the larger the plasticizer for a given difference in solubility parameters, the lower the solubility of the plasticizer. Thus molar volume and differences in solubility parameters determines plasticizer solubility in PVC.

Comparison of Measured Triglyceride Solubility in PVC at 90° C. to Various Plasticizers Some level of solubility in PVC is required such that the plasticizer does not phase separate on aging in PVC causing "spew" on the PVC surface. Additionally, genetically altered organisms like algae and bacteria can produce triglycerides with eight carbon atoms or more.

The preferred plasticizer to displace diisodecyl phthalate (DIDP) in wire and cable applications would have a molecular weight ~446 and have a 90° C. solubility ~160 phr. Solubility molecular weight and the names for various molecules are shown in Table 3. Triglyceride $C_8$ has the right molecular weight but is significantly less soluble than DIDP: 25.8 phr compared to 160 phr for DIDP. A $C_6$ triglyceride could replace dioctyl phthalate (DOP) in lower plasticizer level applications. $C_4$ triglyceride has good solubility but the molecular weight is insufficient for many DOP applications. It could, however, replace dibutyl phthalate (DBP), or butylbenzyl phthalate (BBP) in some applications.

TABLE 3

Measured Solubility in PVC

| Plasticizer | Mw | Phr Measured @ 90° C. |
| --- | --- | --- |
| Triglyceride C2 | 218 | 56.48 |
| Triglyceride C4 | 302 | 232.47 |
| Triglyceride C6 | 387 | 122 |
| Triglyceride C8 | 471 | 25.80 |
| Triglyceride C10 | 555 | 2.45 |
| Triglyceride C12 | 638 | 1.22 |
| Triglyceride C14 | 722 | 1.52 |
| DOP | 392 | 300 |
| DIDP | 446 | 160 |
| TOTM* | 546 | ~80 |
| e-FAME | ~320 | 430 |
| Soy FAME | ~300 | 52 |
| Methyl palmitate | 270 | 10 |
| ESO** | ~950 | 172 |
| Soy oil | ~900 | <1 |

*Trioctyl Trimellitate
**Epoxidized Soy oil

Figure 4:
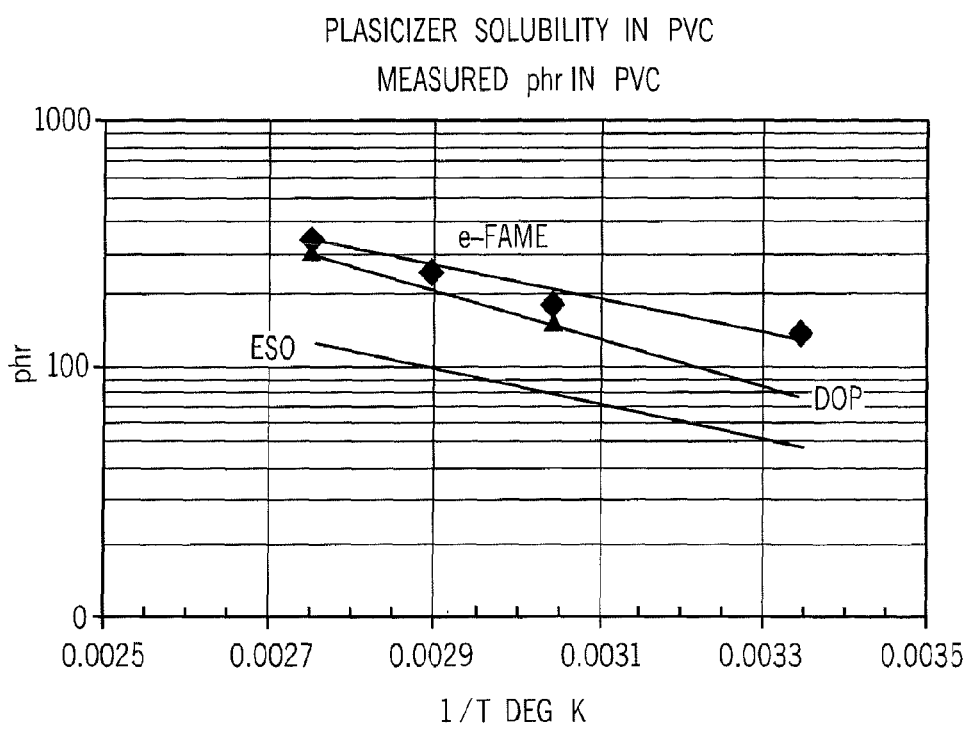
FIG. 4 is a plot reporting the solubility of plasticizers in PVC versus temperature.
Figure 5:
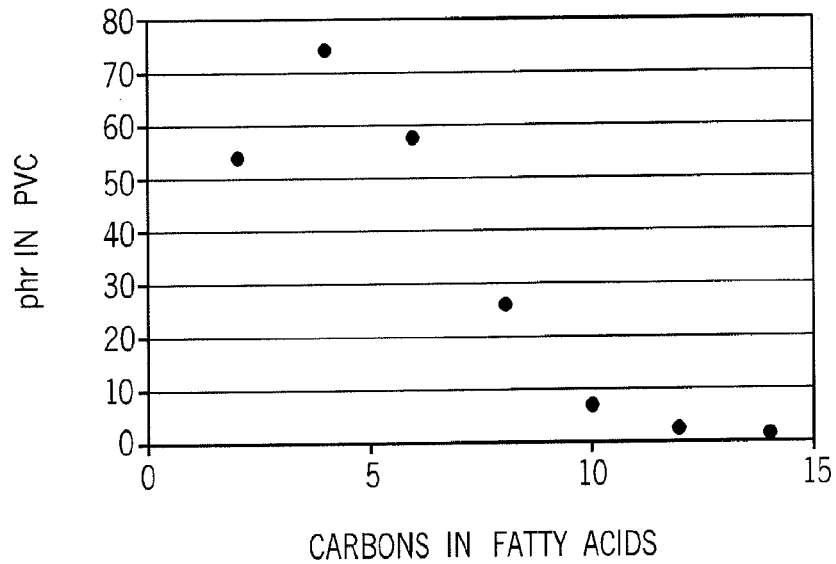
FIG. 5 is a plot reporting the calculated ambient temperature solubility of various triglycerides in PVC versus the number of carbon atoms in the fatty acids.
Figure 6:
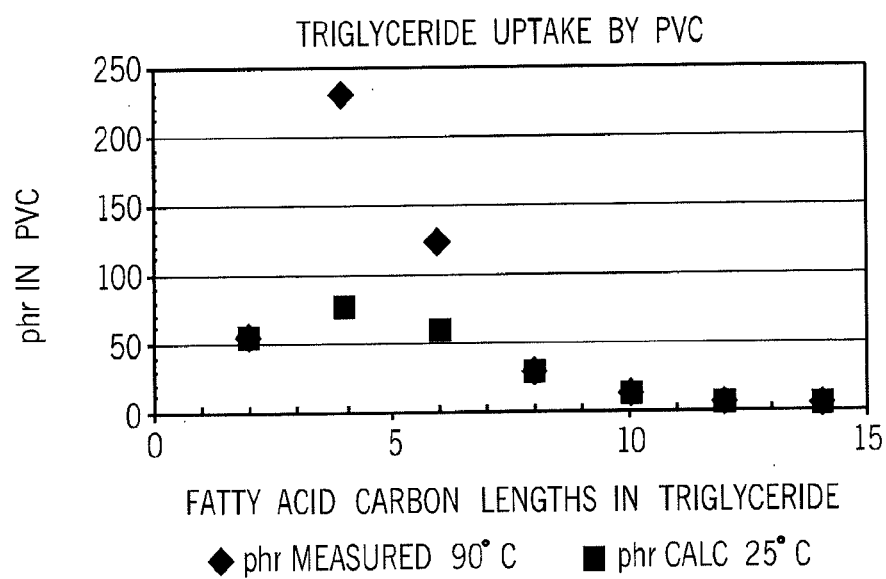
FIG. 6 is a plot comparing the calculated ambient temperature solubility of various triglycerides in PVC against the measured 90° C. solubility of triglycerides in PVC.
Figure 7:
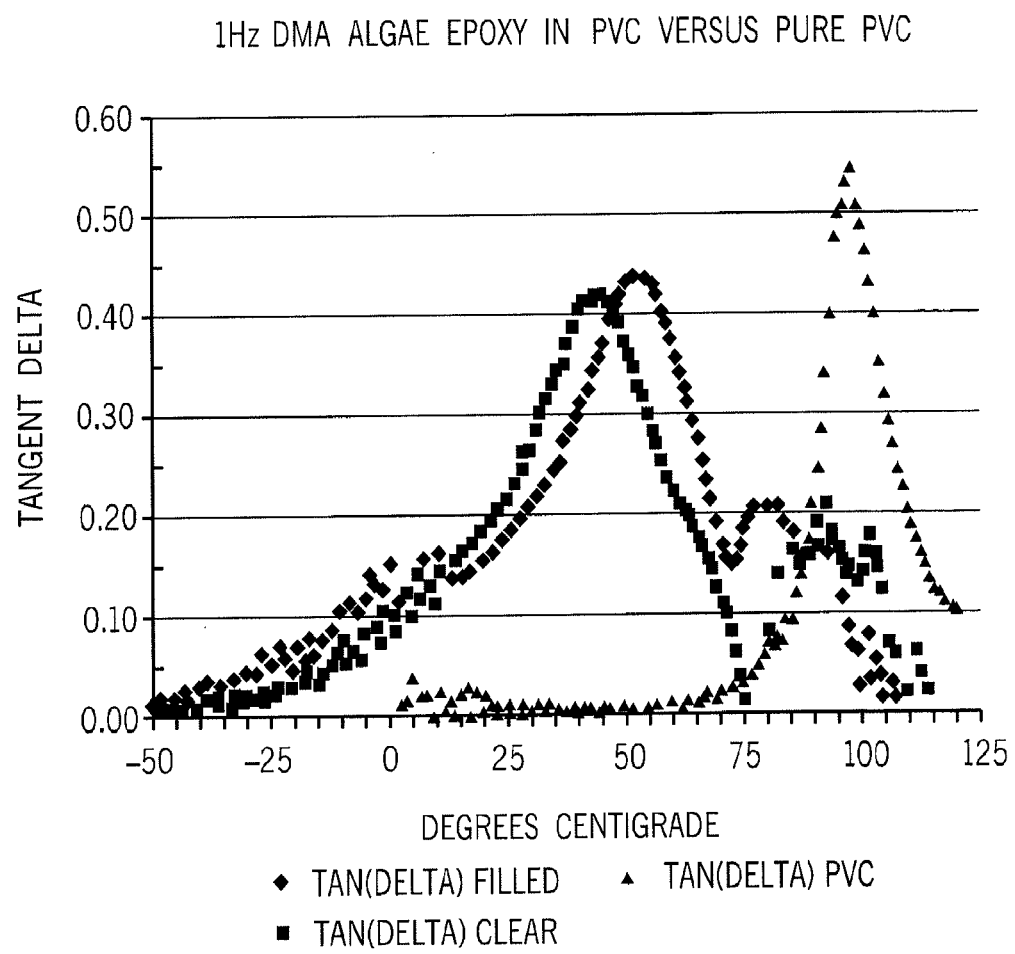
FIG. 7 is a plot reporting the lowering of the glass transition temperature of PVC by the addition of an epoxidized oil extracted from algae.

Of course the plasticizer needs to be soluble in the PVC at ambient and lower temperatures. The solubility of plasticizers in PVC generally decreases as the temperature is decreased (see FIG. 4). Consequently plasticizer solubility at 90° C. is just a rough indicator of the viability of a given molecule as a soluble PVC plasticizer.

Table 3 shows that epoxidizing soy FAME significantly increased the solubility in PVC. Epoxidation increases the polarity of the soy FAME which more closely approaches the solubility parameter of PVC thus increasing the solubility. Additionally soy FAME is more PVC soluble than the saturated methyl palmitate. Of course the unsaturated double bonds in soy FAME will both polymerize at elevated temperature and turn dark brown on oven ageing.

Epoxidation

The following procedure is followed to epoxidize oil extracted from algae:
1. Prepare an ice bath with ice and water.
2. Add 30 g of algae oil to the flask.
3. Add 75 g of $CH_2Cl_2$ to the flask, and begin stirring.
4. Dissolve 44 g of m-chloroperoxybenzoic acid (m-CPBA, 77 wt % purity) in 400 mL CH2Cl2.
5. Add the m-CPBA solution drop-wise to the oil solution, using the ice bath as needed to maintain the temperature below 35° C.
6. After all m-CPBA is added, stir at 35° C. using either an ice bath or heating mantle to maintain the temperature.
7. Monitor reaction progress by iodine titration.
8. After reaction is complete, filter out any salts present.
9. Wash the organic phase by adding 50 ml of 20 wt % $Na_2SO_3$ solution and stirring for 10 minutes.
10 Separate the phases, and return the organic to the flask.
11 Repeat steps 9 and 10.
12. Wash the organic phase by adding 50 ml of 5 wt % $NaHCO_3$ solution and stirring for 10 minutes.
13. Separate the phases, and return the organic to the flask.
14. Repeat steps 12 and 13 until a neutral or basic pH is detected in the aqueous phase.
15. Ad $MgSO_4$ to organic phase to remove residual water.
16. Confirm that all m-CPBA/benzoic acid has been removed by infrared analysis.
17. Remove solvents by rotovapping.
18. Titrate for $I_2$ number.

After epoxidation the color of the algae oil becomes much improved from an initial value of dark red to light yellow. Solubility in PVC, as measured for the pure oil, significantly increases from about 0.4 phr.

To confirm that the epoxidized oil is an effective PVC plasticizer for both clear and filled PVC formulations, the epoxidized oil is melt-mixed in a Brabender bowl mixer at 177° C. to make the formulations reported in Table 4:

TABLE 4

Plasticized PVC Formulations

| Run # | phr PVC | phr Algae Epoxy | phr $CaCO_3$ | phr Metal Soap | phr IRGANOX 1076 |
| --- | --- | --- | --- | --- | --- |
| 1 | 100 | 55 | 68 | 2 | 0.1 |
| 2 | 100 | 50 | 0 | 2 | 0.1 |

The samples are compression molded into plaques approximately 60 mils thick. Modulus versus temperature performance is determined using an AR-1000N dynamic mechanical rheometer, DMA, with solids testing fixtures at 1 Hertz (Hz) in shear. Heating rate of the DMA sample is about one degree Centigrade per minute. Algae oil epoxy samples are compared to a PVC film without plasticizer. The tangent delta peak is taken as the glass transition temperature, Tg, of the polymer at 1 Hz. Clearly the epoxidized algae oil lowers the PVC Tg from about 99° C. for pure PVC to about 55° C. for the filled PVC formulation and about 46° C. for the clear or unfilled PVC formulation.

Although the invention has been described with certain detail through the preceding description of the preferred embodiments, this detail is for the primary purpose of illustration. Many variations and modifications can be made by one skilled in the art without departing from the spirit and scope of the invention as described in the following claims.

What is claimed is:

1. A process for making a plasticizer, consisting essentially of:
   extracting an epoxidized oil from a genetically modified algae, wherein the algae is genetically modified to produce the epoxidized oil, the extracted oil (a) having less than 5 wt % saturated fatty acids and less than 5 wt % fatty acids with 20 or more carbon atoms, (b) comprising triglycerides with unsaturated fatty acids having at least two double bonds, and (c) designed with a balance of hydrophobicity and polarity, and
   converting the extracted oil to the plasticizer without subjecting the extracted oil to epoxidation,
   the plasticizer having
      a solubility in PVC of greater than 40 parts per hundred resin (phr) at 90° C. resulting from the balance of hydrophobicity and polarity, and
      at least one of:
         (i) liquidity at ambient temperature (23° C.),
         (ii) a weight average molecular weight (Mw) of 250 or greater, and
         (iii) an iodine number of 10 or less.

2. The process of claim 1 in which the oil consists essentially of saturated $C_4$ and/or $C_6$ triglycerides.

3. The process of claim 1 in which converting the extracted oil to the plasticizer comprises a purifying process.

4. The process of claim 1 in which the extracted oil comprises unsaturated $C_{12}$ or greater triglycerides, and
   converting the extracted oil to the plasticizer comprises chemically modifying the unsaturated $C_{12}$ or greater triglycerides such that the plasticizer has at least two of the properties (i)-(iii).

5. The process of claim 4 in which chemically modifying the unsaturated $C_{12}$ or greater triglycerides comprises at least one of acylation and transesterification.

6. The process of claim 5 in which the triglycerides are converted to esters of fatty acids by transesterification with one or more alcohols.

7. The process of claim 1 in which the triglycerides with unsaturated fatty acids having at least two double bonds are $C_{16}$ to $C_{20}$ triglycerides.

* * * * *